US008870773B2

(12) United States Patent
Narouze

(10) Patent No.: US 8,870,773 B2
(45) Date of Patent: Oct. 28, 2014

(54) ULTRASOUND-GUIDED DELIVERY OF A THERAPY DELIVERY DEVICE TO A NERVE TARGET

(75) Inventor: Samer Narouze, Akron, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 595 days.

(21) Appl. No.: 12/702,099

(22) Filed: Feb. 8, 2010

(65) Prior Publication Data

US 2010/0204568 A1    Aug. 12, 2010

Related U.S. Application Data

(60) Provisional application No. 61/150,804, filed on Feb. 9, 2009.

(51) Int. Cl.
| | | |
|---|---|---|
| *A61B 8/00* | (2006.01) | |
| *A61B 8/08* | (2006.01) | |
| *A61B 19/00* | (2006.01) | |
| *A61N 1/36* | (2006.01) | |
| *A61N 1/05* | (2006.01) | |
| *A61B 5/00* | (2006.01) | |

(52) U.S. Cl.
CPC ............... *A61B 8/08* (2013.01); *A61B 8/0833* (2013.01); *A61N 1/36017* (2013.01); *A61B 19/50* (2013.01); *A61B 2019/507* (2013.01); *A61B 2019/5276* (2013.01); *A61B 19/201* (2013.01); *A61N 1/36021* (2013.01); *A61N 1/0551* (2013.01); *A61B 5/4893* (2013.01); *A61B 8/0841* (2013.01)
USPC ............ 600/439; 600/407; 600/424; 600/437

(58) Field of Classification Search
USPC .................................. 600/424, 439
See application file for complete search history.

(56) References Cited

U.S. PATENT DOCUMENTS

| | | | | |
|---|---|---|---|---|
| 5,638,819 | A | * | 6/1997 | Manwaring et al. .......... 600/424 |
| 5,788,636 | A | * | 8/1998 | Curley ........................ 600/439 |
| 6,978,787 | B1 | | 12/2005 | Broniatowski |
| 7,069,082 | B2 | | 6/2006 | Lindenthaler |
| 7,277,757 | B2 | | 10/2007 | Casavant et al. |
| 7,651,506 | B2 | * | 1/2010 | Bova et al. .................... 606/130 |

(Continued)

OTHER PUBLICATIONS

Shibata et al., "A New Approach of Ultrasound-Guided Stellate Ganglion Block", *Anesthesia & Analgesia*, 2007; 105:550-551.

(Continued)

*Primary Examiner* — Peter Luong
(74) *Attorney, Agent, or Firm* — Tarolli, Sundheim, Covell & Tummino LLP

(57) ABSTRACT

A method for guiding a therapy delivery device to a sympathetic nerve chain target of a subject includes: (a) selecting a sympathetic nerve chain target; (b) using ultrasound imaging to obtain an ultrasound image of anatomical structures relevant to the sympathetic nerve chain target; (c) determining an implantation pathway based on the ultrasound image, the implantation pathway defining a trajectory that avoids the relevant anatomical structures and extends between an insertion point on the skin of the subject and a bony spinous target; (d) inserting an introducer into the insertion point, the introducer including a bevel located at a distal end thereof; (e) navigating the introducer through the implantation pathway until the distal tip is positioned adjacent or proximate to the bony spinous target; and (f) advancing the therapy delivery device through the introducer to the sympathetic nerve chain target. Steps (d)-(f) are performed using real-time ultrasound imaging.

24 Claims, 7 Drawing Sheets

(56) References Cited

U.S. PATENT DOCUMENTS

| | | | |
|---|---|---|---|
| 7,789,833 B2* | 9/2010 | Urbano et al. | 600/439 |
| 2002/0116030 A1* | 8/2002 | Rezai | 607/9 |
| 2005/0240126 A1 | 10/2005 | Foley et al. | |
| 2007/0016030 A1* | 1/2007 | Stringer | 600/437 |
| 2007/0027483 A1 | 2/2007 | Maschino et al. | |
| 2007/0118183 A1 | 5/2007 | Gelfand et al. | |
| 2007/0150006 A1 | 6/2007 | Libbus et al. | |
| 2007/0179508 A1 | 8/2007 | Arndt | |
| 2008/0064947 A1 | 3/2008 | Heruth et al. | |
| 2008/0119737 A1 | 5/2008 | Urbano et al. | |
| 2008/0208281 A1 | 8/2008 | Tehrani et al. | |
| 2010/0041990 A1* | 2/2010 | Schlitt et al. | 600/439 |

OTHER PUBLICATIONS

Narouze et al., "Ultrasound-Guided Stellate Ganglion Block Successfully Prevented Esophageal Puncture", *Pain Physician*, 2007; 10:747-752.

\* cited by examiner

ULTRASOUND-GUIDED DELIVERY OF A THERAPY DELIVERY DEVICE TO A NERVE TARGET

RELATED APPLICATION

This application claims priority from U.S. Provisional Patent Application Ser. No. 61/150,804, filed Feb. 9, 2009, the subject matter of which is incorporated hereby incorporated by reference in its entirety.

TECHNICAL FIELD

The present invention relates generally to neuromodulatory methods, and more particularly to an ultrasound-guided approach for modulating the activity of a sympathetic nerve chain target.

BACKGROUND OF THE INVENTION

Surgical procedures are often performed by skilled individuals, such as surgeons. Surgeons can perform various surgical procedures based upon their training and past experience, augmented by study of a particular patient. Nevertheless, various portions of a particular patient may be difficult to examine or identify depending upon the area of the anatomy to be examined and the positioning of the patient.

The anatomical structures surrounding the cervical and thoracic ganglia, for example, comprise various critical structures in close proximity to the ganglia. The anatomy surrounding the cervical and thoracic ganglia presents a number of complications potentially associated with access to the ganglia, some of which can be life threatening.

Surgical techniques used to access and treat the cervical and thoracic ganglia (e.g., nerve blockade) have evolved from the use of the standard blind technique to computerized tomography (CT), magnetic resonance imaging (MRI), and radionuclide tracers. These techniques are not practical in clinical practice, however, as they are time consuming, cost-ineffective, and involve radiation exposure. Newer approaches, such as fluoroscopy present a reliable technique for identifying bony structures during surgical access to the cervical and thoracic ganglia. Fluoroscopy cannot, however, identify soft tissue anatomical structures adjacent to bony structures. Consequently, inadvertent needle placement into the vertebral artery, thyroid, thyroid vessels, neural tissues, pleura/lung, or esophagus can occur when using fluoroscopy to access the cervical and/or thoracic ganglia.

SUMMARY OF THE INVENTION

According to one aspect of the present invention, a method is provided for guiding a therapy delivery device to a sympathetic nerve chain target of a subject. One step of the method includes selecting a sympathetic nerve chain (SNC) target. A second step of the method includes using ultrasound imaging to obtain an ultrasound image of anatomical structures relevant to the SNC target. A third step of the method includes determining an implantation pathway based on the ultrasound image. The implantation pathway defines a trajectory that avoids the relevant anatomical structures and extends between an insertion point on the skin of the subject and a bony spinous target. A fourth step of the method includes inserting an introducer into the insertion point. The introducer includes a bevel located at a distal end thereof. A fifth step of the method includes navigating the introducer through the implantation pathway until the distal tip is positioned adjacent or proximate to the bony spinous target. A sixth step of the method includes advancing the therapy delivery device through the introducer to the SNC target. The fourth, fifth, and sixth step of the method are performed using real-time ultrasound imaging.

According to another aspect of the present invention, a method is provided for treating a medical condition in subject. One step of the method includes selecting a SNC target. A second step of the method includes using ultrasound imaging to obtain an ultrasound image of anatomical structures relevant to the SNC target. A third step of the method includes determining an implantation pathway based on the ultrasound image. The implantation pathway defines a trajectory that avoids the relevant anatomical structures and extends between an insertion point on the skin of the subject and a bony spinous target. A fourth step of the method includes inserting an introducer into the insertion point. The introducer includes a bevel located at a distal end thereof. A fifth step of the method includes navigating the introducer through the implantation pathway until the distal tip is positioned adjacent or proximate to the bony spinous target. A sixth step of the method includes advancing the therapy delivery device through the introducer to the SNC target. A seventh step of the method includes applying an electrical current to the SNC target. The fourth, fifth, and sixth step of the method are performed using real-time ultrasound imaging.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
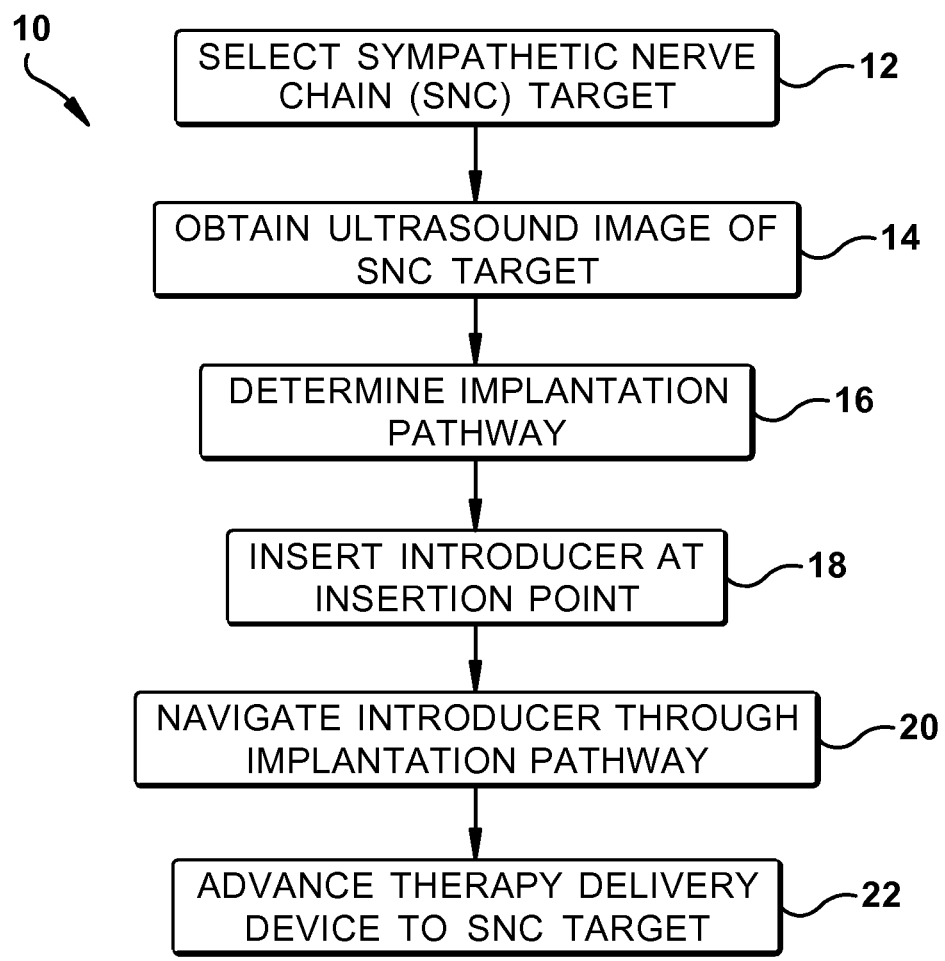
FIG. 1 is a process flow diagram illustrating a method for guiding a therapy delivery device to a sympathetic nerve chain target (SNC) of a subject in accordance with one aspect of the present invention.
Figure 6:
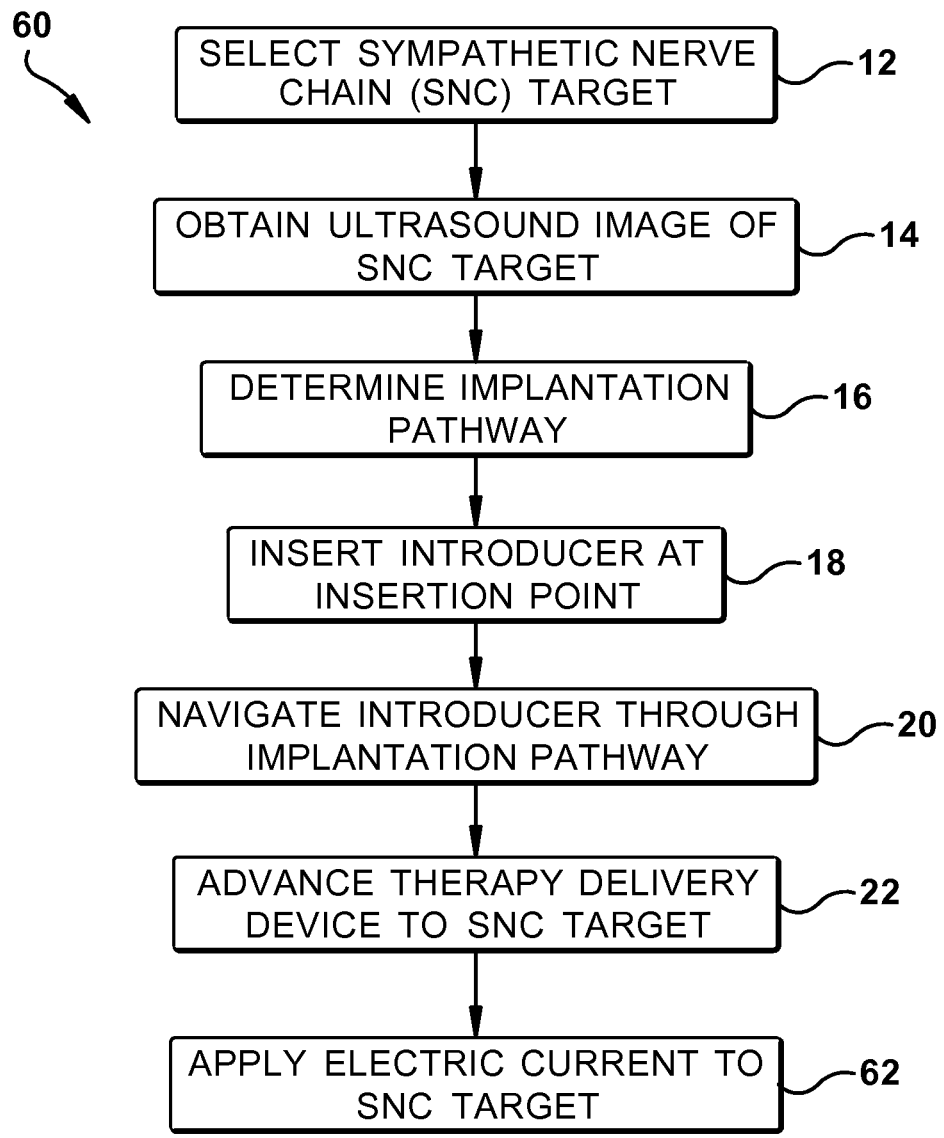
FIG. 6 is a process flow diagram illustrating a method for treating a medical condition in subject in accordance with another aspect of the present invention.

The present invention relates generally to neuromodulatory methods, and more particularly to an ultrasound-guided approach for modulating the activity of a sympathetic nerve chain (SNC) target. As representative of the present invention, FIGS. 1 and 6 illustrate ultrasound-guided methods for delivering a therapy delivery device to a SNC target for treatment of a medical condition in a subject. Unlike prior art methods used to guide therapy delivery devices to SNC targets, which require open surgical dissection and/or inadequate imaging techniques, the present invention takes advantages of ultrasound imaging technology to provide a percutaneous approach for guiding a therapy delivery device to a SNC target. By using ultrasound technology to guide therapy delivery devices, the present invention provides a surgical technique that substantially reduces the risk of damaging critical anatomical structures during placement of a therapy delivery device at a SNC target.

Unless otherwise defined, all technical terms used herein have the same meaning as commonly understood by one of ordinary skill in the art to which the present invention pertains.

In the context of the present invention, the term "medical condition" can refer to any vascular disorder (e.g., stroke) or sympathetically-mediated pain in the upper extremity, head, and/or neck. The term can also refer to movement disorders, epilepsy, cerebrovascular diseases, autoimmune diseases, sleep disorders, autonomic disorders, urinary bladder disorders, abnormal metabolic states, disorders of the muscular system, infectious and parasitic diseases (as provided in ICD-9 codes 1-139), neoplasms (as provided in ICD-9 codes 140-239), endocrine diseases, nutritional and metabolic diseases, immunological diseases (as provided in ICD-9 codes 240-279), diseases of the blood and blood-forming organs (as provided in ICD-9 codes 280-289), mental disorders (as provided in ICD-9 codes 290-319), diseases of the nervous system (as provided in ICD-9 codes 320-359), diseases of the sense organs (as provided in ICD-9 codes 360-389), diseases of the circulatory system (as provided in ICD-9 codes 390-459), diseases of the respiratory system (as provided in ICD-9 codes 460-519), diseases of the digestive system (as provided in ICD-9 codes 520-579), diseases of the genitourinary system (as provided in ICD-9 codes 580-629), diseases of the skin and subcutaneous tissue (as provided in ICD-9 codes 680-709), diseases of the musculoskeletal system and connective tissue (as provided in ICD-9 codes 710-739), congenital anomalies (as provided in ICD-9 codes 740-759), certain conditions originating in the perinatal period (as provided in ICD-9 codes 760-779), and symptoms, signs, and ill-defined conditions (as provided in ICD-9 codes 780-799).

Pain treatable by the present invention can be caused by conditions including, but not limited to, migraine headaches, including migraine headaches with aura, migraine headaches without aura, menstrual migraines, migraine variants, atypical migraines, complicated migraines, hemiplegic migraines, transformed migraines, and chronic daily migraines, episodic tension headaches, chronic tension headaches, analgesic rebound headaches, episodic cluster headaches, chronic cluster headaches, cluster variants, chronic paroxysmal hemicranias, hemicrania continua, post-traumatic headache, post-traumatic neck pain, post-herpetic neuralgia involving the head or face, pain from spine fracture secondary to osteoporosis, arthritis pain in the spine, headache related to cerebrovascular disease and stroke, headache due to vascular disorder, reflex sympathetic dystrophy, cervicalgia (which may be due to various causes, including, but not limited to, muscular, discogenic, or degenerative, including arthritic, posturally related, or metastatic), glossodynia, carotidynia, cricoidynia, otalgia due to middle ear lesion, gastric pain, sciatica, maxillary neuralgia, laryngeal pain, myalgia of neck muscles, trigeminal neuralgia (sometimes also termed tic douloureux), post-lumbar puncture headache, low cerebro-spinal fluid pressure headache, temporomandibular joint disorder, atypical facial pain, ciliary neuralgia, paratrigeminal neuralgia (sometimes also termed Raeder's syndrome); petrosal neuralgia, Eagle's syndrome, idiopathic intracranial hypertension, orofacial pain, myofascial pain syndrome involving the head, neck, and shoulder, chronic migraneous neuralgia, cervical headache, paratrigeminal paralysis, SPG neuralgia (sometimes also termed lower-half headache, lower facial neuralgia syndrome, Sluder's neuralgia, and Sluder's syndrome), carotidynia, vidian neuralgia, causalgia, and/or a combination of the above.

Movement disorders treatable by the present invention may be caused by conditions including, but not limited to, Parkinson's disease, cerebropalsy, dystonia, essential tremor, and hemifacial spasms.

Epilepsy treatable by the present invention may be, for example, generalized or partial.

Cerebrovascular disease treatable by the present invention may be caused by conditions including, but not limited to, aneurysms, strokes, and cerebral hemorrhage.

Autoimmune diseases treatable by the present invention include, but are not limited to, multiple sclerosis.

Sleep disorders treatable by the present invention may be caused by conditions including, but not limited to, sleep apnea and parasomnias.

Autonomic disorders treatable by the present invention may be caused by conditions including, but not limited to, gastrointestinal disorders, including but not limited to gastrointestinal motility disorders, nausea, vomiting, diarrhea, chronic hiccups, gastroesphageal reflux disease, and hypersecretion of gastric acid, autonomic insufficiency; excessive epiphoresis, excessive rhinorrhea; and cardiovascular disorders including, but not limited, to cardiac dysrythmias and arrythmias, hypertension, and carotid sinus disease.

Urinary bladder disorders treatable by the present invention may be caused by conditions including, but not limited to, spastic or flaccid bladder.

Abnormal metabolic states treatable by the present invention may be caused by conditions including, but not limited to, hyperthyroidism or hypothyroidism.

Disorders of the muscular system treatable by the present invention can include, but are not limited to, muscular dystrophy, and spasms of the upper respiratory tract and face.

Neuropsychiatric or mental disorders treatable by the present invention may be caused by conditions including, but not limited to, depression, schizophrenia, bipolar disorder, and obsessive-compulsive disorder.

As used herein, the term "headache" can refer to migraines, tension headaches, cluster headaches, trigeminal neuralgia, secondary headaches, tension-type headaches, chronic and epsisodic headaches, medication overuse/rebound headaches, chronic paroxysmal hemicrinia headaches, hemicranias continua headaches, post-traumatic headaches, post-herpetic headaches, vascular headaches, reflex sympathetic dystrophy-related headaches, crvicalgia headaches, caroidynia headaches, sciatica headaches, trigeminal headaches, occipital headaches, maxillary headaches, cliary headaches, paratrigeminal headaches, petrosal headaches, Sluder's headache, vidian headaches, low CSF pressure headaches, TMJ headaches, causalgia headaches, myofascial headaches, all primary headaches (e.g., primary stabbing headache, primary cough headache, primary exertional headache, primary headache associated with sexual activity, hypnic headache, and new daily persistent headache), all trigeminal autonomic cephalagias (e.g., episodic paroxysmal hemicranias, SUNCT, all probable TACs, and SUNA), chronic daily headaches, occipital neuralgia, atypical facial pain, neuropathic trigeminal pain, and miscellaneous-type headaches.

As used herein, the terms "modulate" or "modulating" can refer to causing a change in neuronal activity, chemistry and/or metabolism. The change can refer to an increase, decrease, or even a change in a pattern of neuronal activity. The terms may refer to either excitatory or inhibitory stimulation, or a combination thereof, and may be at least electrical, biological, magnetic, optical or chemical, or a combination of two or more of these. The terms can also be used to refer to a masking, altering, overriding, or restoring of neuronal activity.

As used herein, the term "subject" can refer to any warm-blooded organism including, but not limited to, human beings, pigs, rats, mice, dogs, goats, sheep, horses, monkeys, apes, rabbits, cattle, etc.

As used herein, the terms "treat" or "treating" shall have their plain and ordinary meaning to one skilled in the art of pharmaceutical or medical sciences. For example, "treat" or "treating" can mean to prevent or reduce a pain in a subject.

FIG. 1 is a process flow diagram illustrating one aspect of the present invention. In FIG. 1, a method 10 is provided for guiding a therapy delivery device 24 (FIGS. 5A-B) to a SNC target (FIG. 2) of a subject. The SNC 27 (FIG. 5B) is part of the sympathetic nervous system and comprises a plurality of interconnected ganglia. The SNC 27 is organized into different sections relative to the cervical, thoracic, lumbar, and sacral sections of the spinal column. The SNC target of the present invention can include any section of the cervical, thoracic, lumbar, or sacral SNC. For example, the SNC target can comprise a cervical ganglion (i.e., superior ganglion, middle ganglion, intermediate ganglion, or inferior ganglion) (not shown), a stellate ganglion 26 (FIG. 2), a T1 ganglion (not shown), a T2 ganglion (not shown), or a T3 ganglion (not shown).

Figure 2:
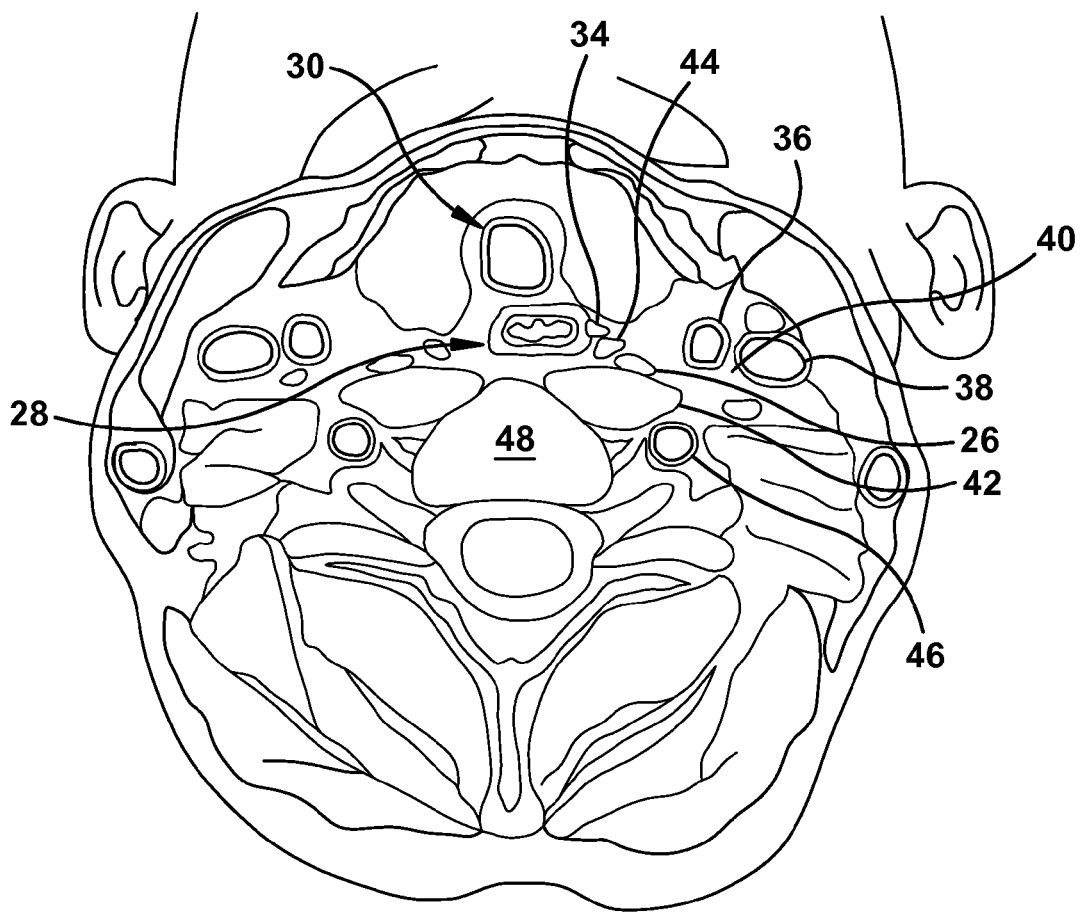
FIG. 2 is a cross-sectional view of a subject taken at the level of C7.

At Step 12 of the method 10 (FIG. 1), a SNC target is selected. The SNC target can be chosen based on a variety of factors, including a particular medical condition or location of the SNC target relative to surrounding anatomical structures. For example, some SNC targets may be appropriate targets for a particular disease, but situated so that they cannot be readily accessed because of tortuous or precarious anatomical structures surrounding (or en route to) the SNC target. Thus, some other SNC target that is more readily accessible may have to be chosen. As described in more detail below, one example of a SNC target can include the stellate ganglion 26 (FIG. 2).

Figure 3:
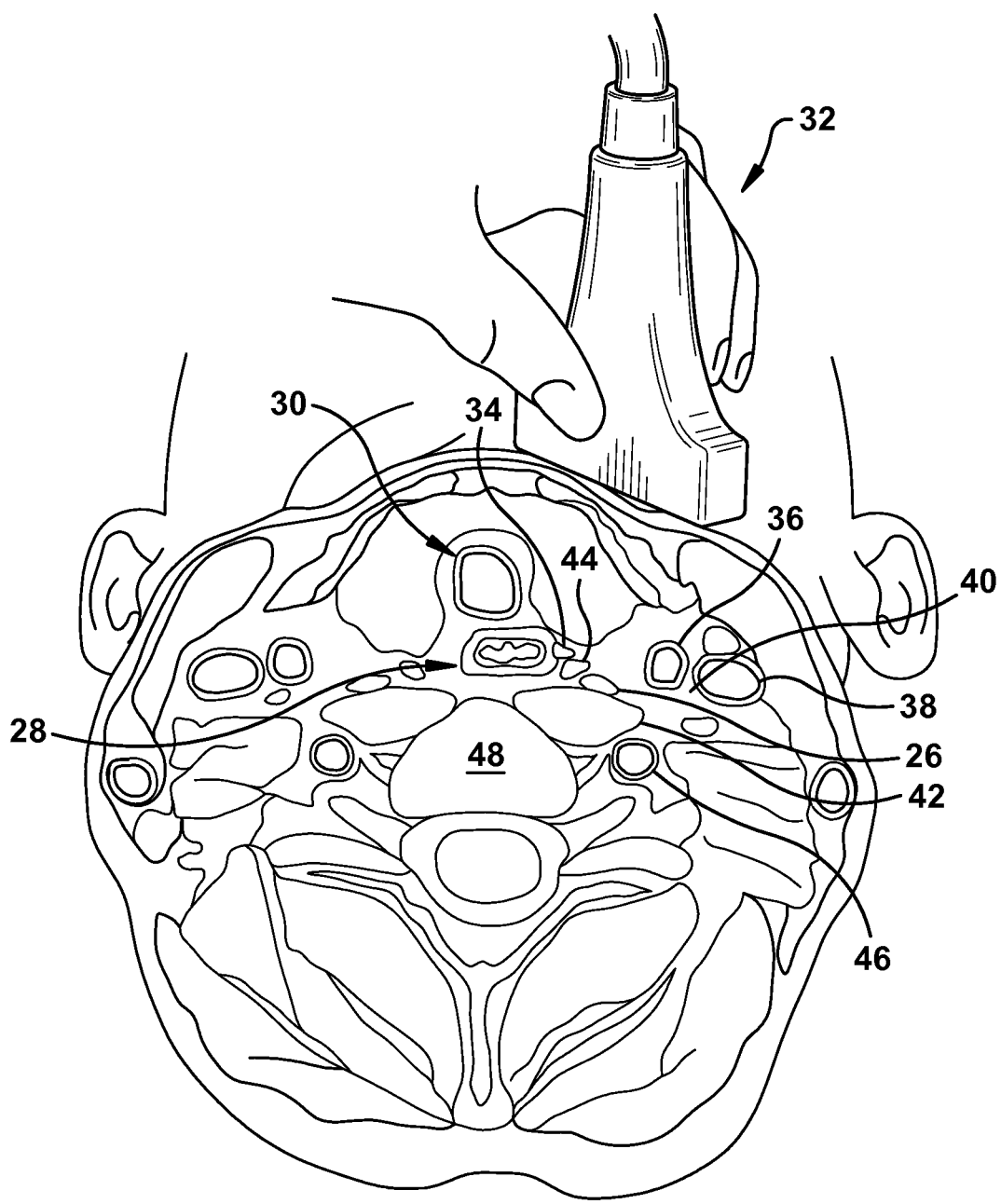
FIG. 3 is a cross-sectional view of the subject in FIG. 2 with an ultrasound transducer placed against the root of the subject's neck.

After selecting a SNC target, an ultrasound image of the anatomical structures relevant to the SNC target is obtained using ultrasound imaging at Step 14. Ultrasound apparatus and related methods for obtaining ultrasound images are known in the art and can include linear or curved array transducers capable of producing, two-, three-, or four-dimensional images. One example of such an apparatus is the Sonosite 180 PLUS ultrasound system (not shown) with an 11-mm broadband (4-7 MHz) tightly curved array transducer (SONOSITE, Bothell, Wash.). Before obtaining the ultrasound image, the subject can be positioned in a supine position with his or her neck extended by placing a pillow under the subject's shoulder to stretch the esophagus 28 so that the esophagus moves medially under the trachea 30. Using aseptic technique, an ultrasound transducer 32 (FIG. 3) is then used to obtain a short axis image of the root of the subject's neck to identify relevant anatomical structures.

Unlike imaging modalities of the prior art used to identify anatomical structures (e.g., fluoroscopy, MRI, CT, etc.), the ultrasound image generated at Step 14 clearly displays important anatomical structures, such as soft tissues, nerves, and vessels. Where the SNC target comprises the stellate ganglion 26, for example, the ultrasound image can identify important anatomical structures including, but not limited to, the trachea 30, the esophagus 28, the recurrent laryngeal nerve 34, the thyroid gland (not shown), the carotid artery 36, the internal jugular vein 38, the vagus nerve 40, the longus coli muscle 42, the inferior thyroid vessels 44, and the vertebral vessels 46.

At Step 16, an implantation pathway is determined based on the ultrasound image obtained at Step 14. The implantation pathway defines a trajectory that avoids the relevant anatomical structures, and extends between an insertion point on the skin of the subject and a bony spinous target. Where the SNC target comprises the stellate ganglion 26, for example, the implantation pathway can be determined by first identifying a bony spinous target, such as C7 48. The level of C7 48 can be identified by the characteristic shape of the transverse process and the position of C7 relative to the vertebral artery 46. After identifying C7 48, a trajectory can be identified that: (1) avoids the relevant anatomical structures along the anterior aspect of the longus coli muscle 42; and (2) extends between an insertion point at the root of the subject's neck and C7.

Figure 4:
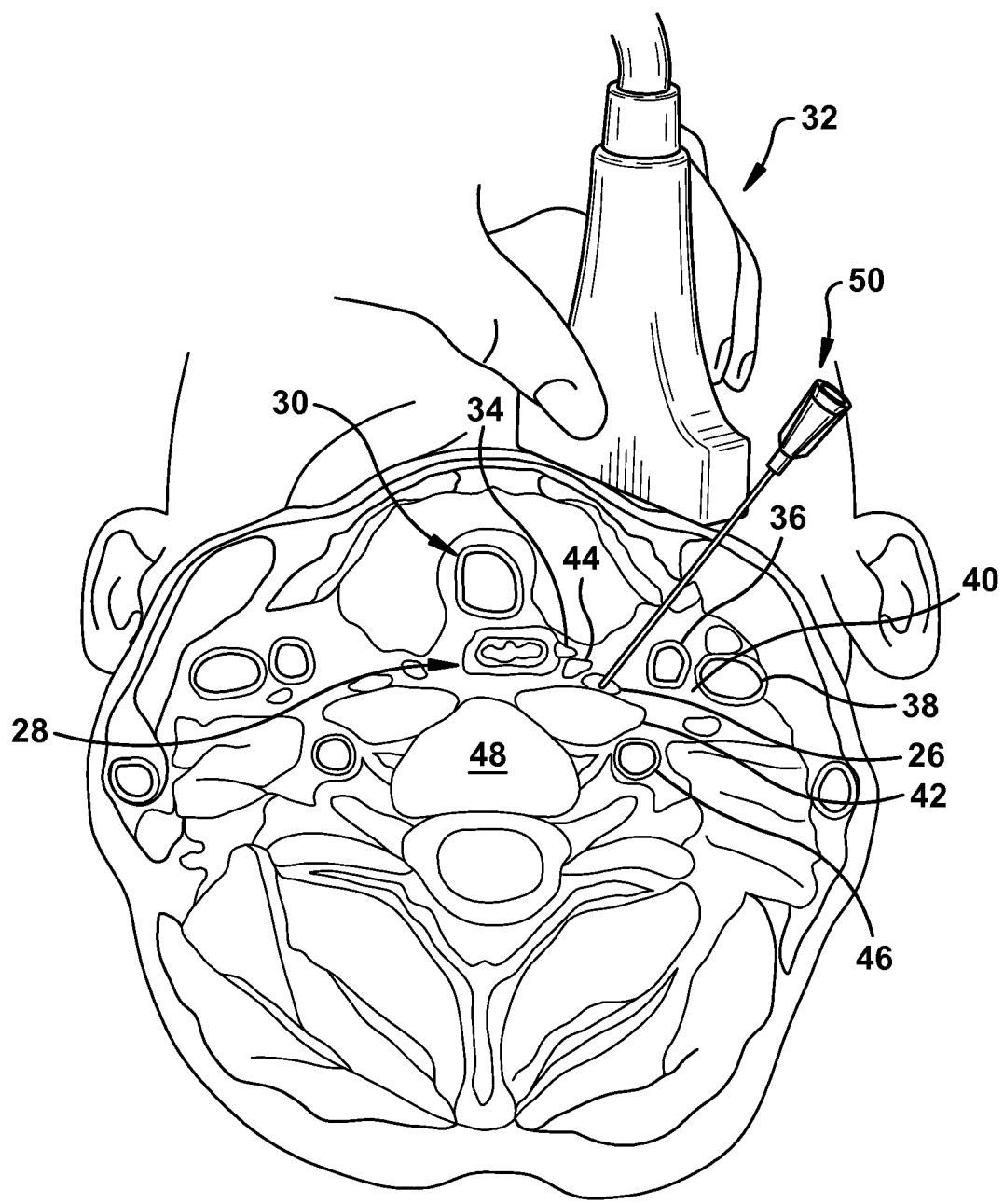
FIG. 4 is a cross-sectional view of the subject in FIG. 3 showing an introducer inserted through an implantation pathway.

Using real-time ultrasound imaging, an introducer 50 (FIG. 4) is inserted into the insertion point at Step 18. The introducer 50 can comprise any device that is capable of tunneling to, and then delivering, a therapy delivery device 24 (FIG. 6) to a SNC target. For example, the introducer 50 (FIG. 4) can comprise a needle having a beveled distal tip (not shown in detail). As shown in FIG. 4, the introducer 50 is inserted into the insertion point using an in-plane or out-of-plane approach to target the anterior aspect of the longus coli muscle 42 where the SNC extends. Navigation of the introducer 50 through the implantation pathway can be stabilized using a securing mechanism (not shown), such as a guide catheter or adhesive tape. At Step 20, the introducer 50 is then navigated through the implantation pathway (e.g., using tactile force) using real-time ultrasound until the distal tip is positioned adjacent or proximate to the bony spinous target (e.g., C7 48). After negative aspiration, placement of the introducer 50 can be checked using real-time fluoroscopy and about 1 ml of contrast agent.

Figure 5A:
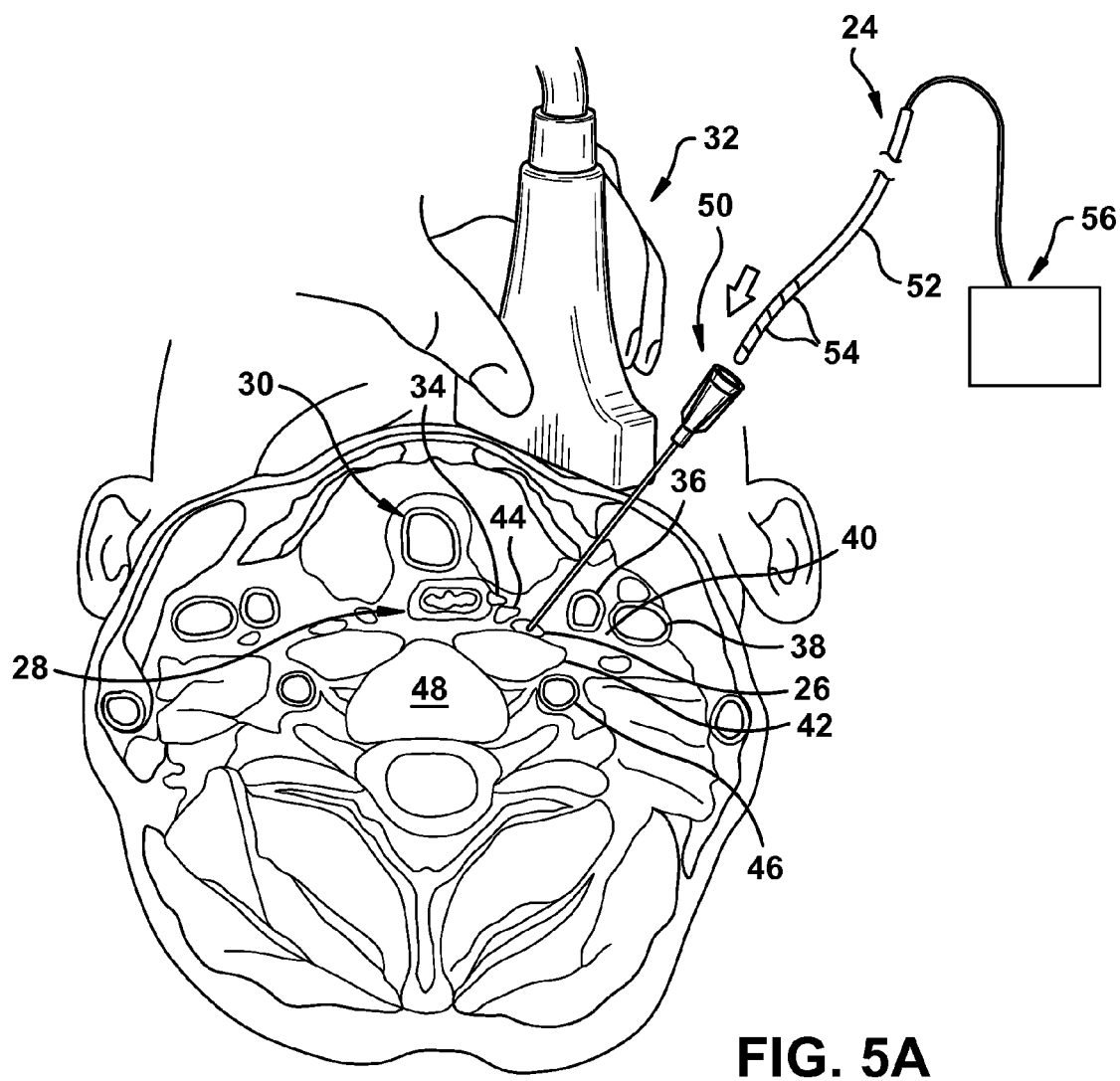
FIG. 5A is a cross-sectional view of the subject in FIG. 4 showing a therapy delivery device being delivered through the introducer to the SNC target.

At Step 22, a therapy delivery device 24 (FIG. 5A) is delivered to the SNC target. The therapy delivery device 24 can include any medical device or apparatus capable of delivering an electrical current to a SNC target. As shown in FIG. 5A, the therapy delivery device 24 can comprise an electrical lead 52 including at least one electrode 54 and being connected to a power source 56. Although the therapy delivery device 24 is shown as being directly connected to the power source 56, it will be appreciated that wireless power sources may also be used to deliver an electric current to the therapy delivery device.

Figure 5B:
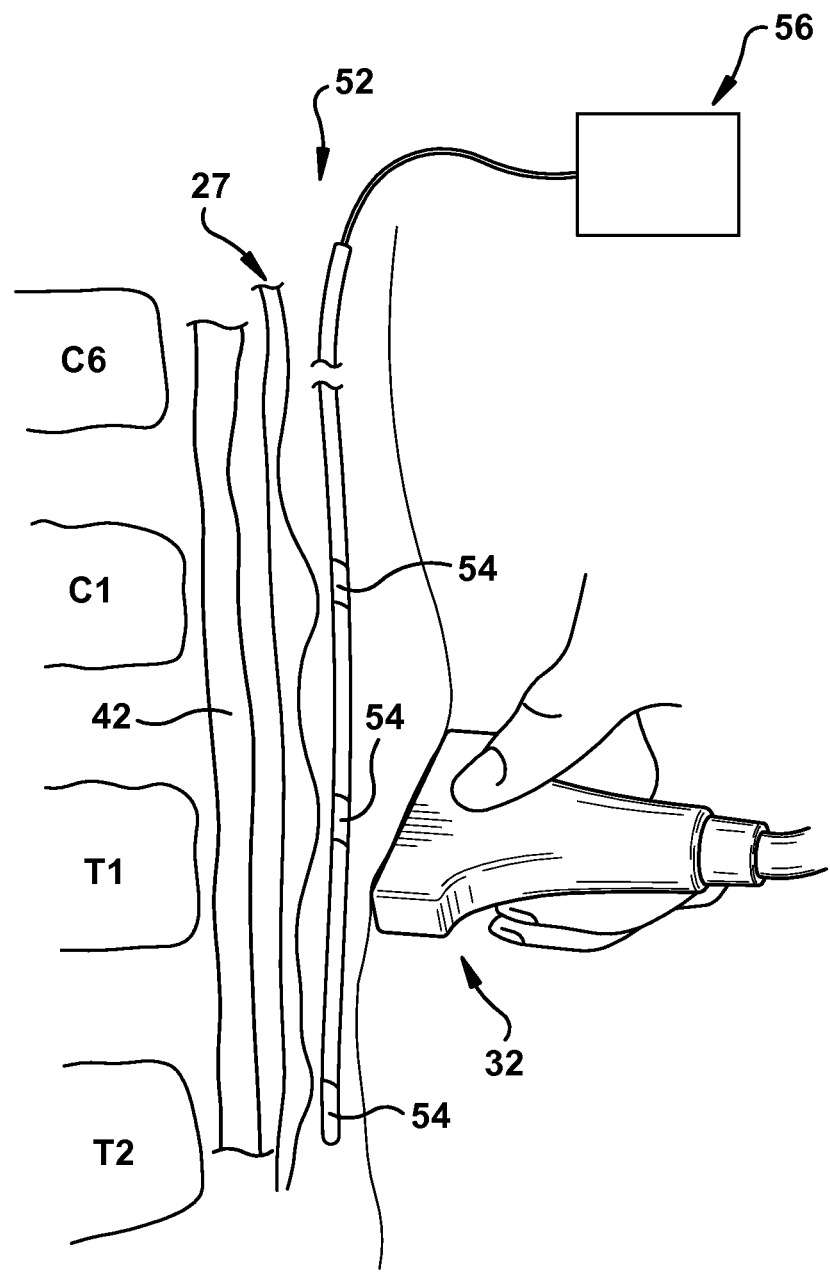
FIG. 5B is a longitudinal axis view showing a therapy delivery device positioned anterior to the longus coli muscle in relation to the sympathetic chain.

The orientation of the introducer 50 can be adjusted depending upon the location of the SNC target. Where the SNC target comprises a middle or superior cervical ganglion, for example, the distal tip of the introducer 50 can be rotated so that the bevel is oriented in a cephalad direction. Alternatively, where the SNC target comprises an inferior cervical ganglion or thoracic ganglion, the distal tip of the introducer 50 can be rotated so that the bevel is oriented in a caudal direction (FIG. 5B). As the therapy delivery device 24 is advanced through the introducer 50, the ultrasound transducer 32 is moved to obtain a longitudinal image and thereby precisely follow advancement of the therapy delivery device in real time.

The present invention take advantage of real-time ultrasound to facilitate placement of therapy delivery devices 24 at SNC targets and thereby minimize the risk of damaging critical anatomical structures when doing so. When delivering a therapy delivery device 24 to the stellate ganglion 24, for example, it is known that the vertebral artery 46 runs anterior to the stellate ganglion at the level of C7 48 before it enters the foramen (not shown) of the C6 transverse process (not shown) in about 90% of cases. In the remaining cases, however, the vertebral artery 46 enters at C5 (not shown) or higher. This makes the vertebral artery 46 vulnerable to injury at the level of both C6 and C7 48. Using ultrasound, however, can mitigate this possibility by enabling visualization of both bony structures (i.e., C6 and C7 48) and vascular structures (i.e., the vertebral artery 46) during placement of therapy delivery devices 24. Similarly, the inferior thyroid vessels 44 run ventrally at the level of C6 and C7 48. The inferior thyroid vessels 44, together with the thyroid gland, have been reported to be a source of retropharyngeal hematoma with stellate ganglion block. Using fluoroscopic guidance, for example, the thyroid gland and inferior thyroid vessels 44 can be easily injured in the path of the introducer 50. Using ultrasound, however, can mitigate this possibility by enabling visualization of vascular structures (i.e., the inferior thyroid vessels 44) during placement of therapy delivery devices 24.

FIG. 6 is a process flow diagram illustrating another aspect of the present invention. In FIG. 6, a method 60 is provided for treating a subject with a medical condition. Although the method 60 will be described below in terms of treating a subject with complex regional pain syndrome (CRPS), it will be appreciated that the method can be used to treat any one or combination of medical conditions described herein.

The steps of the method 60 are substantially identical to Steps 12-22 of the method 10 (FIG. 1) above, except where described below. For example, the method 60 (FIG. 6) can begin by selecting an SNC target at Step 12. To treat a subject suffering from CRPS, the stellate ganglion 24 can be selected for neuromodulation. After selecting the stellate ganglion 24 as the SNC target, an ultrasound image of the anatomical structures relevant to the stellate ganglion can be obtained at Step 14. For example, an ultrasound transducer 32 can be used to obtain a short axis image of the root of the subject's neck. The ultrasound image can then be used to identify critical anatomical structures, such as the trachea 30, esophagus 28, recurrent laryngeal nerve 34, thyroid gland, carotid artery 36, internal jugular vein 38, vagus nerve 40, longus coli muscle 42, inferior thyroid vessels 44, the vertebral vessels 46, nerve roots, and spinal cord.

At Step 16 of the method 60, an implantation pathway can be determined based on the ultrasound image. Where the SNC target comprises the stellate ganglion 24, the implantation pathway can be determined by first identifying a bony spinous target, such as C7 48. The level of C7 48 can be identified by the characteristic shape of the transverse process and the position of C7 relative to the vertebral artery 46. After identifying C7 48, a trajectory can be identified that: (1) avoids the relevant anatomical structures along the anterior aspect of the longus coli muscle 42; and (2) extends between an insertion point at the root of the subject's neck and C7 48.

Using real-time ultrasound, an introducer 50 can be inserted into the insertion point at Step 18. The introducer 50 can comprise a needle having a beveled distal tip, for example. The introducer 50 can be inserted at the insertion point using an in-plane or out-of-plane approach to target the anterior aspect of the longus coli muscle 42 where the SNC extends. Navigation of the introducer 50 through the implantation pathway can be stabilized using a securing mechanism (not shown), such as a guide catheter or adhesive tape. At Step 20, the introducer 50 can be navigated through the implantation pathway (e.g., using tactile force) using real-time ultrasound until the distal tip is positioned adjacent or proximate to the bony spinous target (e.g., C7 48). After negative aspiration, placement of the introducer 50 can be checked using real-time fluoroscopy and about 1 ml of contrast agent.

At Step 22, a therapy delivery device 24 can be delivered to the SNC target (FIGS. 5A-B). As shown in FIG. 5A, the therapy delivery device 24 can comprise an electrical lead 52 including at least one electrode 54 and being connected to a power source 56. The distal tip of the introducer 50 can then be rotated so that the bevel is oriented towards the SNC target. With the bevel appropriately positioned, the electrical lead 52 can then be advanced through the introducer 50 (indicated by arrow) under real-time ultrasound until at least one electrode 54 of the electrical lead is positioned adjacent or proximate to the stellate ganglion 24.

At Step 62, the power source 56 can be activated so that an electrical current is passed through the electrical lead 52 and into the stellate ganglion 24. The electrical current may be episodic, continuous, phasic, in clusters, intermittent, upon demand by the subject or medical personnel, or pre-programmed to respond to a sensor (not shown) (e.g., a closed-loop system). The electrical current can be operated at a constant voltage (e.g., at about 0.1 v to about 25 v), at a constant current (e.g., at about 25 microampes to about 50 milliamps), at a constant frequency (e.g., at about 5 Hz to about 10,000 Hz), and at a constant pulse-width (e.g., at about 50 μsec to about 10,000 μsec). Application of the electrical current can be monopolar, bipolar, or multipolar, depending upon the polarity of the electrical lead 52. The waveform may be, for example, biphasic, square wave, sine wave, or other electrically safe and feasible combinations. Additionally, the electrical current may be applied to the SNC target (i.e., the stellate ganglion) simultaneously or sequentially.

Delivery of electrical current to the stellate ganglion 24 can suppress the pain experienced by the subject by "blocking" nerve impulse transmission through the stellate ganglion. As unregulated and increased nerve transmission is essential for the body to propagate and recognize pain, blocking nerve impulse transmissions through the stellate ganglion 24 can diminish the pain experienced by the subject. Upon delivery of the electrical current to the electrical lead 52, the subject may be asked to report any pain sensation. The position of the electrical lead 52, or frequency of electrical current being delivered to the electrical lead, may then be adjusted until the subject reports experiencing diminished pain sensation and/or autonomic changes in the head and/or upper extremities, lungs, and heart are observed. Once satisfactory, the electrical lead 52 can be self-anchored or anchored to the deep tissues and then tunneled to an infraclavicular area (not shown) where an IPG (not shown) can be implanted.

From the above description of the invention, those skilled in the art will perceive improvements, changes and modifications. For example, it will be appreciated that the therapy delivery device 24 can comprise a drug infusion catheter (not shown) or a drug infusion system (not shown), examples of which are known in the art. Such improvements, changes, and modifications are within the skill of the art and are intended to be covered by the appended claims.

Having described the invention, I claim:

1. A method for guiding a therapy delivery device to a sympathetic nerve chain target of a subject, said method comprising the steps of:

(a) selecting a sympathetic nerve chain target;

(b) using ultrasound imaging to obtain an ultrasound image of anatomical structures relevant to the sympathetic nerve chain target;

(c) determining a pre-determined implantation pathway, prior to inserting an introducer into an insertion point, based on the ultrasound image generated in step (b), the pre-determined implantation pathway defining a trajectory that avoids the relevant anatomical structures and extends between the insertion point on the skin of the subject and a bony spinous target;
(d) inserting the introducer into the insertion point;
(e) navigating the introducer through the pre-determined implantation pathway until the distal tip is positioned adjacent or proximate to the bony spinous target; and
(f) advancing the therapy delivery device through the introducer to the sympathetic nerve chain target;
wherein steps (d)-(f) are performed using real-time ultrasound imaging.

2. The method of claim 1, wherein the sympathetic nerve chain target is selected from the group consisting of a cervical ganglion, a stellate ganglion, a T1 ganglion, a T2 ganglion, and a T3 ganglion.

3. The method of claim 1, wherein said step of using ultrasound imaging to obtain an ultrasound image further comprises the step of:
obtaining a short axis ultrasound image of the root of the subject's neck; and
identifying a plurality of anatomical structures selected from the group consisting of the trachea, the esophagus, the recurrent laryngeal nerve, the thyroid gland, the carotid artery, the internal jugular vein, the vagus nerve, the longus coli muscle, the inferior thyroid vessels, the vertebral vessels, and the sympathetic nerve chain.

4. The method of claim 3 wherein said step of identifying a plurality of anatomical structures locates the pre-determined implantation pathway so as to avoid the plurality of anatomical structures along an anterior aspect of a longus coli muscle and extend between an insertion point at the root of the subject's neck and a bony spinous target at a level of C7.

5. The method of claim 1, wherein said step of determining an implantation pathway further comprises identifying a bony spinous target at a level of C7.

6. The method of claim 1, wherein said step of navigating the introducer through the implantation pathway further comprises providing a securing mechanism to stabilize the introducer during navigation through the implantation pathway.

7. The method of claim 1, wherein said step of navigating the introducer through the implantation pathway further comprises using an in-plane or out-of-plane approach to target the anterior aspect of a longus coli muscle.

8. The method of claim 1, wherein said step of navigating the introducer through the implantation pathway further comprises the steps of:
directing a bevel of the introducer caudally; and
advancing the therapy delivery device through the introducer until the therapy delivery device is positioned adjacent or proximate to at least one of a stellate ganglion, a T1 ganglion, a T2 ganglion, or a T3 ganglion.

9. The method of claim 1, wherein said step of navigating the introducer through the implantation pathway further comprises the steps of:
directing the bevel of the introducer in a cephalad direction; and
advancing the therapy delivery device through the introducer until the therapy delivery device is positioned adjacent or proximate to at least one of a stellate ganglion or a cervical ganglion.

10. The method of claim 1, wherein the implantation pathway is determined prior to step (d).

11. The method of claim 1, wherein steps (a)-(f) are performed sequentially.

12. A method for treating a medical condition in a subject, said method comprising the steps of:
(a) selecting a sympathetic nerve chain target;
(b) using ultrasound imaging to obtain an ultrasound image of anatomical structures relevant to the sympathetic nerve chain target;
(c) determining a pre-determined implantation pathway, prior to inserting an introducer into an insertion point, based on the ultrasound image obtained in step (b), the pre-determined implantation pathway defining a trajectory that avoids the relevant anatomical structures and extends between the insertion point on the skin of the subject and a bony spinous target;
(d) inserting the introducer into the insertion point;
(e) navigating the introducer through the pre-determined implantation pathway until the distal tip is positioned adjacent or proximate to the bony spinous target;
(f) advancing the therapy delivery device through the introducer to the sympathetic nerve chain target; and
(g) applying an electrical current to the sympathetic nerve chain target;
wherein steps (d)-(f) are performed using real-time ultrasound imaging.

13. The method of claim 12, wherein said step of applying an electrical current to the sympathetic nerve chain target further comprises applying a sufficient amount of electrical current to substantially block nerve conduction at the sympathetic nerve chain target.

14. The method of claim 13, wherein said step of applying a sufficient amount of electrical current to substantially block nerve conduction includes blocking nerve conduction to alleviate pain.

15. The method of claim 12, wherein the sympathetic nerve chain target is selected from the group consisting of a cervical ganglion, a stellate ganglion, a T1 ganglion, a T2 ganglion, and a T3 ganglion.

16. The method of claim 12, wherein said step of using ultrasound imaging to obtain an ultrasound image further comprises the step of:
obtaining a short axis ultrasound image of the root of the subject's neck; and
identifying a plurality of anatomical structures selected from the group consisting of the trachea, the esophagus, the recurrent laryngeal nerve, the thyroid gland, the carotid artery, the internal jugular vein, the vagus nerve, the longus coli muscle, the inferior thyroid vessels, the vertebral vessels, and the sympathetic nerve chain.

17. The method of claim 14, wherein said step of identifying a plurality of anatomical structures locates the pre-determined implantation pathway so as to avoid the plurality of anatomical structures along an anterior aspect of a longus coli muscle and extend between an insertion point at the root of the subject's neck and a bony spinous target at a level of C7.

18. The method of claim 12, wherein said step of determining an implantation pathway further comprises identifying a bony spinous target at a level of C7.

19. The method of claim 12, wherein said step of navigating the introducer through the implantation pathway further comprises providing a securing mechanism to stabilize the introducer during navigation through the implantation pathway.

20. The method of claim 12, wherein said step of navigating the introducer through the implantation pathway further comprises using an in-plane or out-of-plane approach to target an anterior aspect of a longus coli muscle.

21. The method of claim 12, wherein said step of navigating the introducer through the implantation pathway further comprises the steps of:
directing a bevel of the introducer caudally; and advancing the therapy delivery device through the introducer until the therapy delivery device is positioned adjacent or proximate to at least one of a stellate ganglion, a T1 ganglion, a T2 ganglion, or a T3 ganglion.

22. The method of claim 12, wherein said step of navigating the introducer through the implantation pathway further comprises the steps of:
   directing the bevel of the introducer in a cephalad direction; and
   advancing the therapy delivery device through the introducer until the therapy delivery device is positioned adjacent or proximate to at least one of a stellate ganglion or a cervical ganglion.

23. The method of claim 12, wherein said step of applying an electrical current to the sympathetic nerve chain target further comprises delivering an amount of electrical current sufficient to prevent or mitigate an acute medical condition.

24. A method for guiding a therapy delivery device to a cervical or thoracic sympathetic nerve chain target of a subject, said method comprising the steps of:
   (a) selecting a sympathetic nerve chain target;
   (b) generating an ultrasound image that identifies the thyroid gland, the inferior thyroid vessels, and the vertebral artery, the ultrasound image being generated by obtaining a short axis ultrasound image of the root of the subject's neck;
   (c) generating a pre-determined implantation pathway, prior to inserting an introducer into an insertion point, based on the ultrasound image generated in step (b), the pre-determined implantation pathway defining a trajectory that avoids the thyroid gland, the inferior thyroid vessels, and the vertebral artery and extends between the insertion point on the skin of the subject and a bony spinous target;
   (d) inserting the introducer into the insertion point, the introducer including a bevel located at a distal end thereof;
   (e) navigating the introducer through the pre-determined implantation pathway until the distal tip is positioned adjacent or proximate to the bony spinous target;
   (f) directing the bevel of the introducer either caudally or in a cephalad direction;
   (g) advancing the therapy delivery device through the introducer to the cervical or thoracic sympathetic nerve chain target;
   wherein steps (d)-(g) are performed using real-time ultrasound imaging;
   wherein steps (a)-(g) are performed sequentially.

* * * * *